United States Patent
Emery

(10) Patent No.: US 6,402,693 B1
(45) Date of Patent: Jun. 11, 2002

(54) ULTRASONIC TRANSDUCER ALIGNING SYSTEM TO REPLICATE A PREVIOUSLY OBTAINED IMAGE

(75) Inventor: Charles Emery, Renton, WA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/482,744

(22) Filed: Jan. 13, 2000

(51) Int. Cl.[7] .................................................. A61B 8/00

(52) U.S. Cl. ...................................................... 600/443

(58) Field of Search ................................. 600/437, 443, 600/447; 128/916

(56) References Cited

U.S. PATENT DOCUMENTS

| | | | | |
|---|---|---|---|---|
| 3,556,079 A | * | 1/1971 | Omizo | 600/461 |
| 5,181,513 A | * | 1/1993 | Toboul | 600/443 |
| 6,012,458 A | * | 1/2000 | Mo et al. | 128/916 |
| 6,152,878 A | * | 11/2000 | Nachtomy et al. | 600/467 |
| 6,159,152 A | * | 12/2000 | Sumanaweera et al. | 600/443 |

* cited by examiner

Primary Examiner—Francis J. Jaworski

(57) ABSTRACT

To aid a physician or sonographer in replicating an image of tissue sample, an ultrasound machine performs a comparison of ultrasound images with a stored reference image. The results of the comparison are provided to a user in a visual or audible form to allow the user to alter the position of the transducer to substantially match the position used to acquire the reference image.

7 Claims, 2 Drawing Sheets

Saved Image   New Image

ULTRASONIC TRANSDUCER ALIGNING SYSTEM TO REPLICATE A PREVIOUSLY OBTAINED IMAGE

FIELD OF THE INVENTION

The present invention relates to medical imaging systems in general, and ultrasound imaging systems in particular.

BACKGROUND OF THE INVENTION

In diagnostic medical imaging, it is often necessary to view the same tissue sample at different times. For example, in stress tests, a physician may compare recorded images of the heart at rest to real time images of the heart under stress in order to detect the presence of disease. Similarly, in order to detect any growth of a tumor it is useful to compare images of the tumor taken at various time intervals.

Ultrasound is becoming an increasingly common technique for non-invasively imaging body tissue or blood flow. In order to obtain similar images of a tissue sample, it is necessary that the ultrasound probe that transmits ultrasonic signals into the body and receives corresponding echo signals be oriented in substantially the same direction for each image. In the past, a physician or sonographer would typically make a handwritten note in a file concerning the position of a transducer. This would be used as a guide to placing the transducer the next time an image of a tissue sample is to be obtained. Alternatively, if subsequent images are to be taken in a relatively short amount of time, the physician may outline the position of the transducer on the patient with a felt-tip pen. Both these techniques allow only rudimentary alignment of the transducer and therefore can make it difficult to compare images of the tissue sample that are taken at different points in time.

SUMMARY OF THE INVENTION

To improve the ability of a physician or sonographer to duplicate the orientation of an ultrasonic transducer, a reference image is obtained and stored on a recordable medium. The reference image contains a tissue sample that is to be compared with later acquired images of the tissue sample. To orient the transducer in the same direction used to obtain the reference image, subsequent images are compared against the reference image. Results of the comparison are fed back to the user so that the transducer position can be moved to obtain a higher degree of similarity with the reference image.

In one embodiment of the invention, the comparison is performed as a sum of absolute differences wherein the intensity of each pixel in the reference image is subtracted from the intensity of a corresponding pixel in a subsequent image. The sum over the entire set of pixels in the reference and subsequent image is used to provide feedback to the user so that the user knows if the transducer orientation is becoming more or less like the orientation used to obtain the reference image. Once a subsequent image is obtained having a high degree of similarity, the subsequent image is stored and compared against the reference image so that a physician or sonographer may determine how the tissue sample changes over time or with stress, etc.

DETAILED DESCRIPTION OF THE PREFERRED EMBODIMENT

The present invention is a method for helping a user duplicate a previously recorded ultrasound image by replicating the alignment of an ultrasound transducer in order to obtain sequential images of a tissue sample from a nearly identical position.

Figure 1:
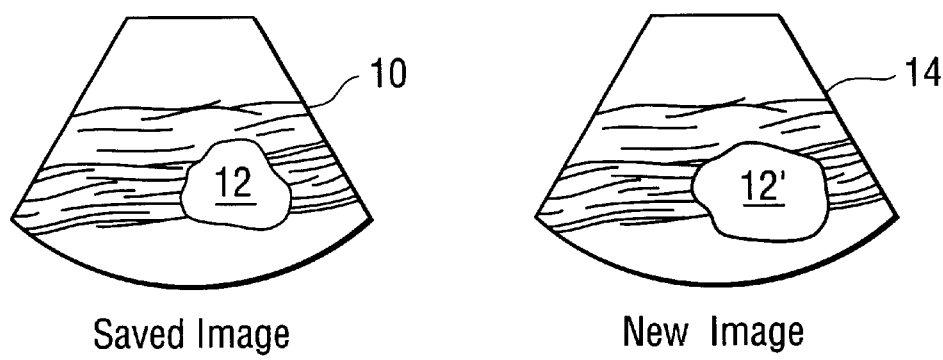
FIG. 1 illustrates two sequentially obtained ultrasound images of a tissue sample to be compared over time.

FIG. 1 illustrates a pair of sequentially obtained ultrasound images. A reference image 10 contains a tissue sample 12 that is of interest to a physician or sonographer. For example, the tissue sample 12 may be a heart muscle in a non-stressed condition or may be an image of a tumor located in the patient's body. In order to analyze the tissue sample under different conditions, such as stress, or at a different time, a subsequent ultrasound image 14 is obtained. In the subsequent image 14, the tissue sample 12' is seen under the different conditions or at a different time. In order to accurately compare the tissue sample 12 with the later image of the tissue sample 12', it is necessary that the ultrasound images 10 and 14 be obtained with a transducer that is aligned in substantially the same direction with respect to the patient's body. As indicated above, it has generally been difficult to replicate the alignment of an ultrasound transducer. Therefore, most sonographers or physicians can only position a transducer in approximately the same orientation which may make a tissue sample appear different in each image and therefore difficult to quantify how the sample varies over time or under different conditions.

Figure 2:
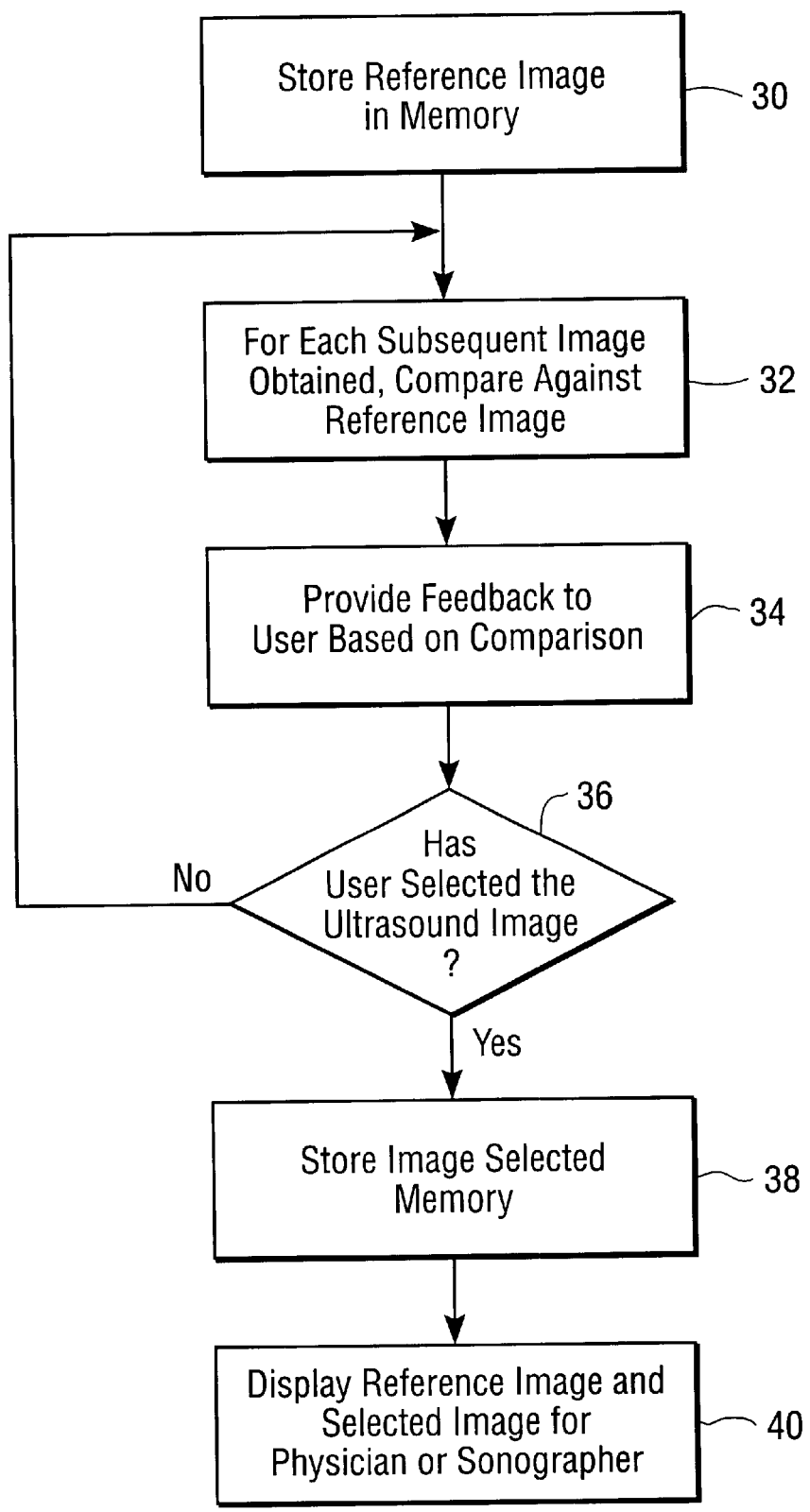
FIG. 2 illustrates a series of steps performed by one embodiment of the present invention in order to align a transducer.

FIG. 2 illustrates a series of steps performed by one embodiment of the present invention in order to allow a physician or sonographer to replicate the orientation of an ultrasound transducer.

Beginning with a step 30, a user of the ultrasound system selects a reference image against which future images will be compared. The reference image is stored on a recordable media of the ultrasound system. The media may be an electronic memory or may be a computer-readable magnetic memory such as a hard disk, floppy disk, video tape, optical disk, etc. When the user wishes to obtain another image of the tissue sample in the reference image, the user positions the probe at approximately the same location used to obtain the reference image and begins acquiring sequential ultrasound images. For each subsequent image obtained, a computer processor within the ultrasound system computes a two-dimensional comparison with the reference image stored in memory. At a step 34, the user is provided with feedback indicating the results of the comparison for each image. The comparison may produce an audible tone that varies in frequency or loudness with the degree of similarity between the two images. Alternatively, the feedback may comprise a visual display that changes in appearance or intensity with the degree of similarity. By responding to the feedback, the user can tell whether the image is becoming more or less like the reference image. Upon achieving an acceptable degree of similarity, the user knows that the orientation of the transducer is nearly the same as that used to obtain the reference image.

At a step 36, it is determined whether the user has selected a subsequent image for comparison against the reference image. If not, the processing returns to step 32 and additional images are obtained and compared against the reference image. If the answer to step 36 is yes, then the image selected is stored on the recordable media at a step 38. At a step 40, the reference image and the selected subsequent image are displayed for a physician or sonographer in order to compare the tissue sample under different conditions or at different times.

In the presently preferred embodiment of the invention, the comparison performed comprises a sum of absolute differences (SAD) calculation performed on each pixel of the reference image with each pixel of the subsequently obtained images. The magnitude of each pixel of the reference image and a corresponding pixel in a subsequent image are subtracted and summed over the entire image. Those images having a higher degree of similarity will have a lower sum. Therefore, the ultrasound system provides feedback to the user indicating the results of the SAD calculation. Although the presently preferred embodiment of the invention uses the SAD technique, other two dimensional correlation techniques could be used. For example, the two images may be compared using correlation, mean brightness, 2-D Fourier transform, least mean squares, median or mode techniques or other mathematical techniques that provide an indication of the similarity of the two images. A 2-D cross-correlation technique provides not only a measure of the similarity between the two images but also provides data indicating which way the subsequent image (and hence which way the transducer should be moved) to increase the similarity of the images. Furthermore, it is not required that the comparison be based on the whole image. Instead, a user may select a portion of the image that is compared against additional images.

Figure 3:
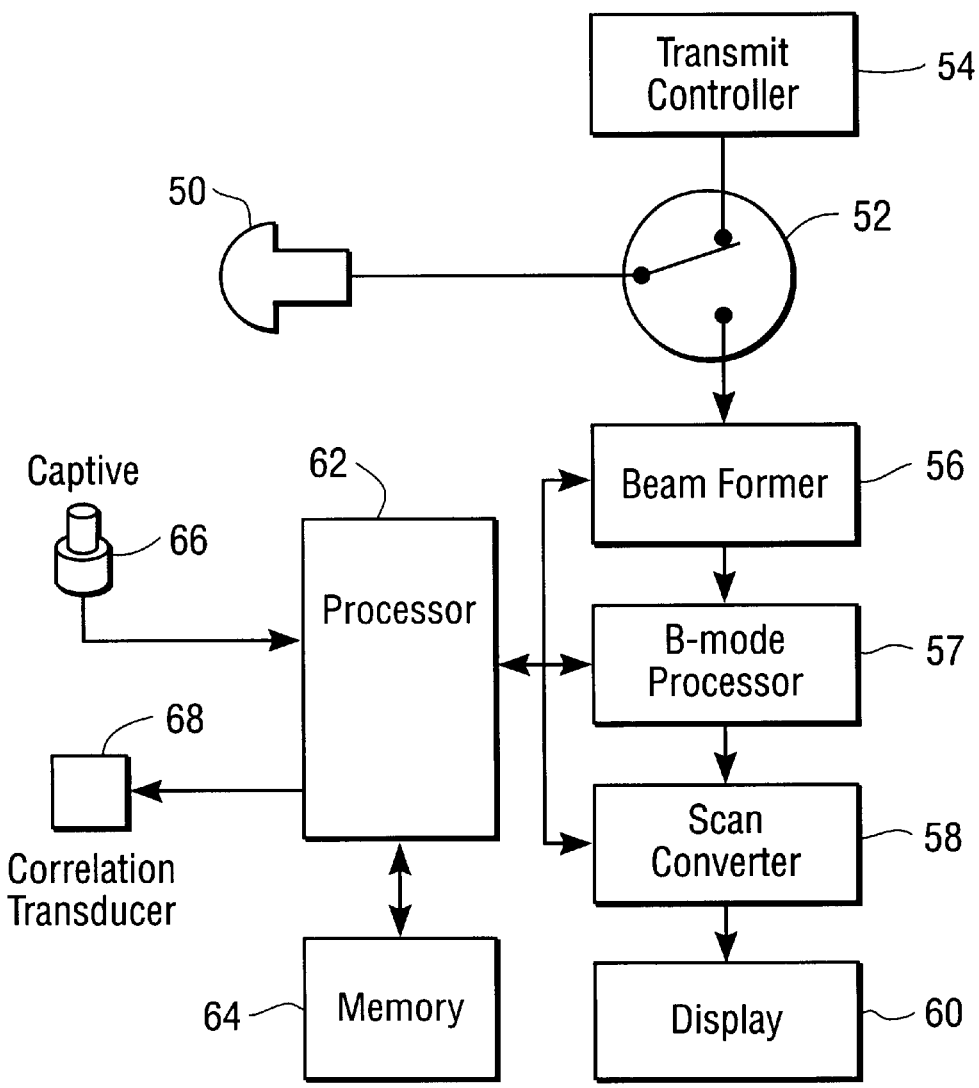
FIG. 3 illustrates a block diagram of an ultrasound system that operates according to the present invention.

FIG. 3 is a block diagram of an ultrasound system that operates in accordance with the present invention. An ultrasound transducer 50 is connected to a transmit/receive switch 52. In one position, the transmit/receive switch 52 connects the transducer 50 to a transmit controller 54 that supplies a series of electronic signals that cause the transducer 50 to deliver an ultrasonic pulse to the patient. Echo signals created by scatterers in the patient's body in response to the pulses transmitted are received by the transducer 50. The transducer 50 converts the received echo signals to corresponding electronic echo signals. When receiving echo signals, the position of the transmit/receive switch 52 is changed so that the electronic echo signals are supplied to a beamformer 56 that combines the electronic echo signals into a single signal representative of the size or density of a scatterer at a particular point in the patient's body. The output of the beamformer 56 is applied to a B-mode processor 57, which assembles echo signals received on a member of receive beam lines into an ultrasound image. The image data from the B-mode processor 57 is supplied to a scan converter 58 that converts the data from the B-mode processor into a format suitable for display on a video monitor 60 for viewing by a physician or sonographer.

In addition to supplying the scan converter with data, the ultrasound data produced by the B-mode processor is also supplied to a computer processor 62 which stores data for individual images in a memory 64. The processor 62 is interfaced with a capture switch 66 or other input device which allows a user to indicate when an image frame is to be saved. The physician or sonographer selects an image frame for use as a reference frame against which future ultrasound images will be compared. Once a reference frame has been stored in a memory 64, subsequent frames are compared with the reference frame by the processor 62. A signal which is proportional to the comparison is supplied to a transducer 68, which provides a visual or audible indication of the degree of similarity to the user. Once the degree of similarity has reached an acceptable level, the user selects the capture switch 66 or speaks, a command which is interpreted and causes the processor 62 to store the latest image frame in the memory 64. Alternatively, the ultrasound system may always store the subsequent image having the greatest degree of similarity without user input. After the reference frame and the subsequent frame have been stored in the memory, they can be displayed for the user on the video monitor 60 in order to allow the physician or sonographer to compare the tissue sample in the image. As an alternative to performing the comparison in the processor 62, the B-mode processor 57 may contain a digital signal processor (DSP) or other programmable hardware to do the comparison. Furthermore, it is not necessary that the images that are compared against the reference image are obtained in real time. For example, the images could be obtained from a sequence of images (a cine sequence). A user makes one image in the cine sequence and the ultrasound system selects a later image from the sequence having the greatest degree of similarity. Finally, the present invention is not limited to use with B-mode images, but could be used with any ultrasound imaging mode such as Doppler, power mode, color, THI, etc.

As can be seen from the above, the present invention provides feedback to the user concerning the orientation of a transducer in order to allow a user to more accurately replicate a previously obtained ultrasound image.

The embodiments of the invention in which an exclusive property or privilege is claimed are defined as follows:

1. A method of replicating the alignment of an ultrasound transducer comprising:
   obtaining a reference ultrasound image;
   storing the reference ultrasound image;
   obtaining a series of sequential ultrasound images;
   for each sequential ultrasound image, comparing at least part of the sequential ultrasound image with at least part of the reference ultrasound image;
   selecting a subsequent image having a high degree of similarity to the reference image; and
   providing feedback to the user, the feedback being a function of a degree of similarity.

2. The method of claim 1, wherein the reference ultrasound image was obtained with a transducer in a first position, further comprising:
   obtaining the subsequent ultrasound images with a transducer; and
   providing feedback to a user that is dependent upon the comparison to allow the user to adjust the orientation of the ultrasound transducer to substantially match the first position.

3. The method of claim 2, wherein the feedback is provided to the user by:
   providing an audible signal, the sound of which is dependent on the comparison of the reference image and a subsequently obtained ultrasound image.

4. The method of claim 2, wherein the feedback is provided to the user by:
   providing a visual indication the appearance of which is dependent on the comparison of the reference image and the subsequently obtained image.

5. The method of claim 1, further comprising:
   selecting a portion of the reference image for comparison with a portion of the series of sequential ultrasound images.

6. An ultrasound system, comprising:
   an ultrasound transducer for transmitting ultrasound pulses into a patient and generating electronic echo signals in response to received echo signals;

a beamformer that receives the electronic echo signals and focuses them;

an image processor that receives the focused echo signals and produces an ultrasound image;

a processor that stores an ultrasound image as a reference image and compares the reference image with subsequently produced ultrasound images; and a feedback mechanism that produces an indication that is dependent on the correlation of an ultrasound image with the reference image, such that a user can adjust the position of the ultrasound transducer based on the correlation.

7. A method of replicating the alignment of an ultrasound transducer the method comprising:

(a) obtaining a reference ultrasound image;

(b) comparing a subsequent ultrasound image to the reference ultrasound image;

(c) determining a degree of similarity with a processor as a function of (b); and (d) adjusting an orientation of the ultrasound transducer as a function of the degree of similarity.

* * * * *